United States Patent [19]
Weiser

[11] Patent Number: 5,713,958
[45] Date of Patent: Feb. 3, 1998

[54] INTRAOCULAR IMPLANT DEVICE FOR CORRECTING OCULAR ANISOTROPY

[75] Inventor: Marc Weiser, Paris, France

[73] Assignee: W.K. et Associes, Paris, France

[21] Appl. No.: 664,380

[22] Filed: Jun. 14, 1996

[30] Foreign Application Priority Data

Jun. 22, 1995 [FR] France ................... 95 07477

[51] Int. Cl.⁶ ................................................. A61F 2/16
[52] U.S. Cl. ................................................. 623/6
[58] Field of Search ....................................... 623/6

[56] References Cited

U.S. PATENT DOCUMENTS

| | | | |
|---|---|---|---|
| 4,118,808 | 10/1978 | Poler | 623/6 |
| 4,149,279 | 4/1979 | Poler | 623/6 |
| 4,249,272 | 2/1981 | Poler | 623/6 |
| 4,434,515 | 3/1984 | Poler | 623/6 |
| 4,657,546 | 4/1987 | Shearing | 623/6 |
| 4,892,543 | 1/1990 | Turley | 623/6 |
| 5,092,880 | 3/1992 | Ohmi | 623/6 |
| 5,171,266 | 12/1992 | Wiley et al. | 623/6 |
| 5,628,795 | 5/1997 | Langerman | 623/6 |

FOREIGN PATENT DOCUMENTS

| | | |
|---|---|---|
| 0 528 325 A1 | 2/1993 | European Pat. Off. . |
| 0 650 704 A1 | 5/1995 | European Pat. Off. . |
| A 62 254889 | 4/1989 | Japan . |
| WO A 94 07435 | 4/1994 | WIPO . |

Primary Examiner—Mary Beth Jones
Attorney, Agent, or Firm—Wolf, Greenfield & Sacks, P.C.

[57] ABSTRACT

An intraocular implant device for correcting ocular anisotropy, and in particular astigmatism, the device having a haptic portion and an optic portion that is substantially circular in shape and suitable for correcting the anisotropy in a diametral direction. The optical portion and the haptic portion are constituted by two different parts. The haptic portion has a first end suitable for co-operating with the inside wall of the eye when the implant device is placed in the eye for the purpose of holding the optical portion in position, and a second end suitable for cooperating with the periphery of the optical portion to provide the optical portion with rotary guidance about its optical axis. The haptic portion also prevents the optical portion from moving in translation relative to the haptic portion, and further includes a braking feature for allowing the optical portion to rotate only under the effect of a torque being applied to the optical portion.

13 Claims, 6 Drawing Sheets

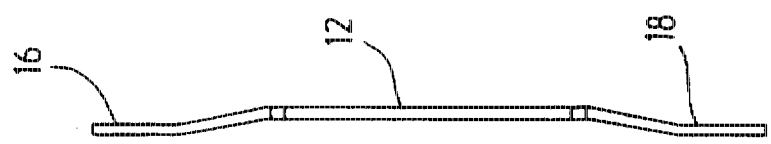
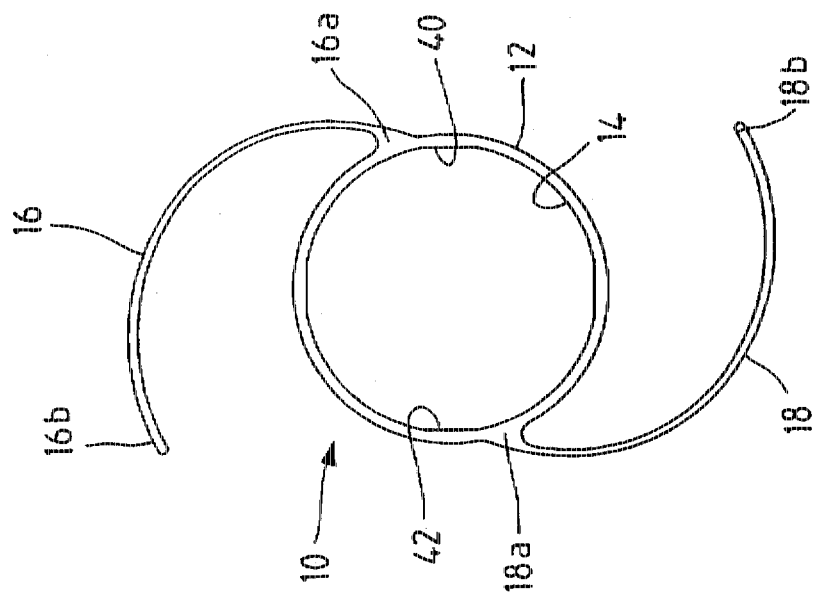
FIG. 1b
FIG. 1a

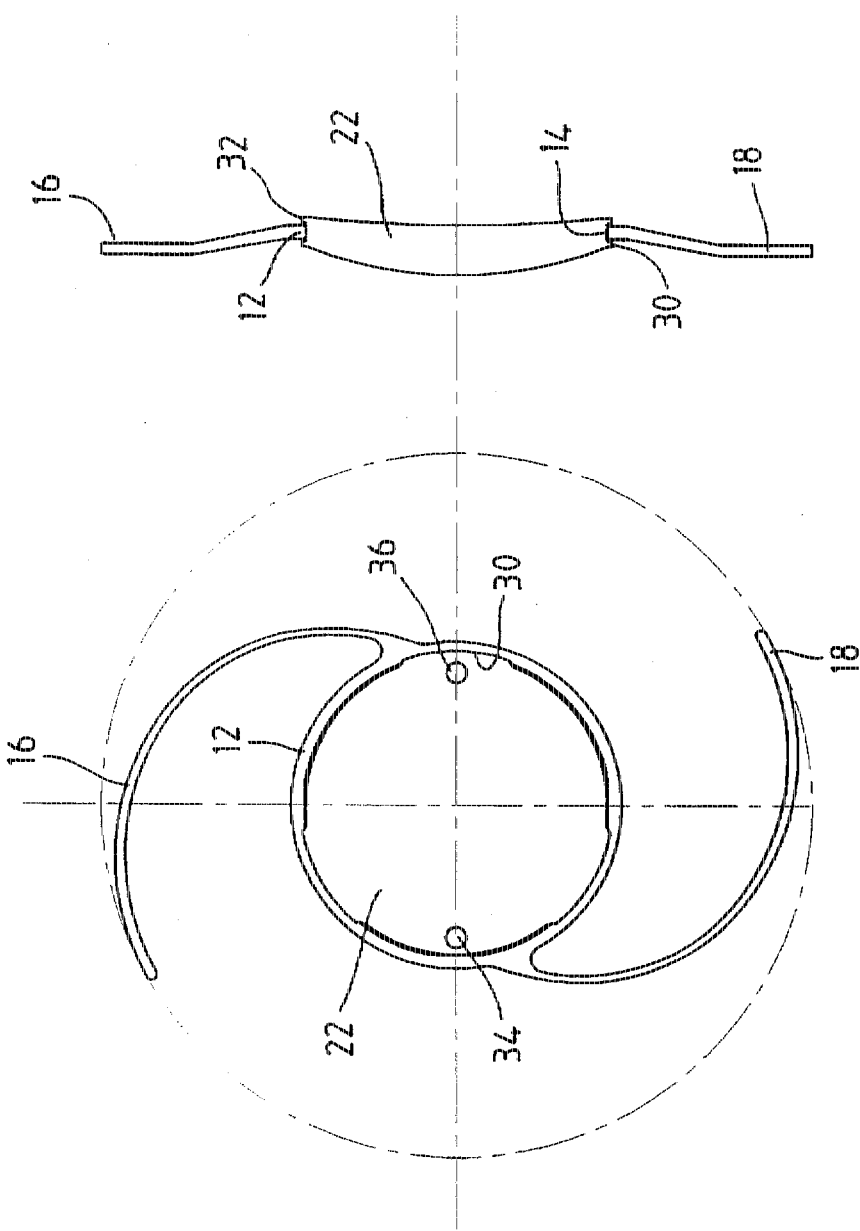

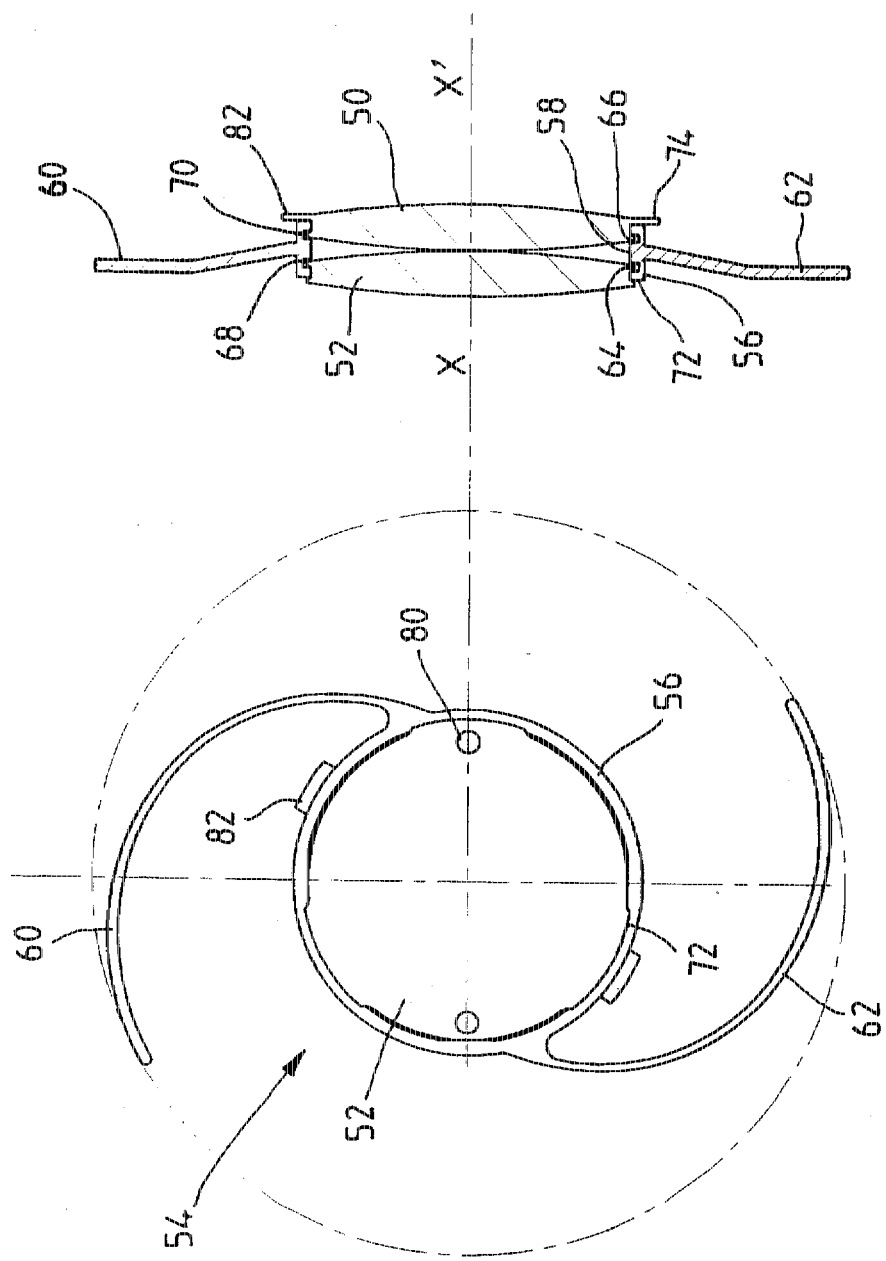

INTRAOCULAR IMPLANT DEVICE FOR CORRECTING OCULAR ANISOTROPY

The present invention relates to an intraocular implant device for correcting ocular anisotropy.

BACKGROUND OF THE INVENTION

Throughout the present text, the term "ocular anisotropy" is used to cover any type of defect in the operation of the eye which causes the image perceived thereby to lose circular symmetry about the optical axis of the eye. In other words, this term is used to cover any situation in which the image of an object as received by the retina in various diametral directions of the eye relative to its optical axis is not of the same size or does not have the same focus, thereby giving rise to differences of sharpness. This type of vision defect is present in particular in the form of astigmatism which corresponds to defective radii of curvature of the cornea. As is well known, such astigmatism can be "natural", i.e. pre-operative, or on the contrary it can be post-operative, i.e. the result of making an incision in the eye.

It will be understood that to correct such a vision defect, it is necessary to have an optical correcting system which itself presents anisotropic optical correction in radial directions relative to the optical axis of the correcting system. Intraocular implants having faces shaped in such a manner as to provide such an anisotropic correction to sight are well known. Under such circumstances, the two faces of the intraocular implant lens are combinations of surfaces that are spherical, cylindrical, toroidal, or even conical.

It will be understood that in order to install such a correcting optical system, it is essential for the angular positioning of the optical system to be accurately determined relative to the eye so that the optical correction does indeed compensate the vision defect. This result is easily obtained when the correction is provided by a pair of spectacles in which the lenses are in angular positions that are accurately determined relative to the eyes to be corrected.

In contrast, with intraocular implants, the situation is quite different. An intraocular implant is constituted by an optical portion constituted essentially by a correcting lens and by a haptic portion whose periphery co-operates with the inside wall of the eye, e.g. that of the capsular sac, to hold the optical portion in position in such a manner that the optical axis thereof coincides substantially with the optical axis of the eye containing the implant. It is difficult to give an intraocular implant a very accurate angular orientation while it is being put into place in the eye, in particular because of the elasticity required of the haptic portion which can give rise to a certain rotary torque being applied to the optical portion after it has been put into place, thereby altering its angular position. Another difficulty lies in the fact that after the implant has been put into place in the eye, the periphery of the haptic portion can slide relative to the inside wall of the eye, e.g. under the effect of a shock received by the eye. It turns out that even in the anterior chamber of the eye, or more usually in the capsular sac, the effect of capsular symphysis or of synechia which enables the end of the haptic portion to become fixed to the wall of the eye develops only after a certain amount of time has elapsed since the date of implantation, which time can be of the order of 2 to 3 months. It will also be understood that after these phenomena have occurred, it is not longer possible to perform a further intervention to readjust the angular position of the intraocular implant. As a result, the risk of the implant being wrongly positioned, angularly, are very high.

OBJECTS AND SUMMARY OF THE INVENTION

An object of the present invention is to provide an intraocular implant serving to correct ocular anisotropy and making it possible for the implant to be angularly positioned in an accurately determined manner.

To achieve this object, the invention provides an intraocular implant device for correcting ocular anisotropy and in particular astigmatism, the device comprising a haptic portion and an optical portion that is substantially circular in shape and suitable for correcting the anisotropy in a diametral direction, wherein said optical portion and said haptic portion are constituted by two different parts, wherein said haptic portion has a first end suitable for co-operating with the inside wall of the eye when the implant device is disposed in the eye for the purpose of holding said optical portion in position, and a second end suitable for co-operating with the periphery of said optical portion to define rotary guidance means for said optical portion about its optical axis, means for preventing the optical portion moving in translation relative to said haptic portion along the optical axis, and braking means for allowing the optical portion to rotate only under the effect of applying to the optical portion a torque of magnitude greater than a predetermined value.

It will be understood that because of the architecture of the implant, once the haptic portion has become fixed to the inside wall of the eye, and in particular to the capsular sac, thereby preventing the optical portion from rotating, it is possible to perform a minor surgical intervention to rotate the optical portion relative to the haptic portion in controlled manner so as to bring the optical portion into the required angular position. Because of the braking means, it will be understood that the angular position will be maintained without risk of modification.

In a first implementation of the invention, the optical portion is constituted by a single lens that is mounted to rotate in the haptic portion, said single lens having a diametral direction for correcting the anisotropy.

In an improved embodiment, the optical portion of the implant is constituted by two separate lenses, whose optical axes coincide and which can be rotated independently. After the haptic portion has become fixed, it is possible surgically to modify the angular position of the various lenses, not only to adapt the diametral direction of correction applied to optical anisotropy, but also to modify the power of the correction by adapting the relative angular position of the two lenses.

BRIEF DESCRIPTION OF THE DRAWINGS

Other characteristics and advantages of the invention appear better on reading the following description of various embodiments of the invention given as non-limiting examples. The description refers to the accompanying figures, in which:

FIGS. 1a and 1b are respectively a front view and a side view of an embodiment of the haptic portion when the implant has a single lens only;

FIGS. 3a and 3b are respectively a front view and a side view of a complete intraocular implant constituting a first embodiment of an implant having a single lens;

FIGS. 4a and 4b show a second embodiment of the implant respectively in front view and in diametral section for an implant that has two separate lenses;

MORE DETAILED DESCRIPTION

Figure 1C:
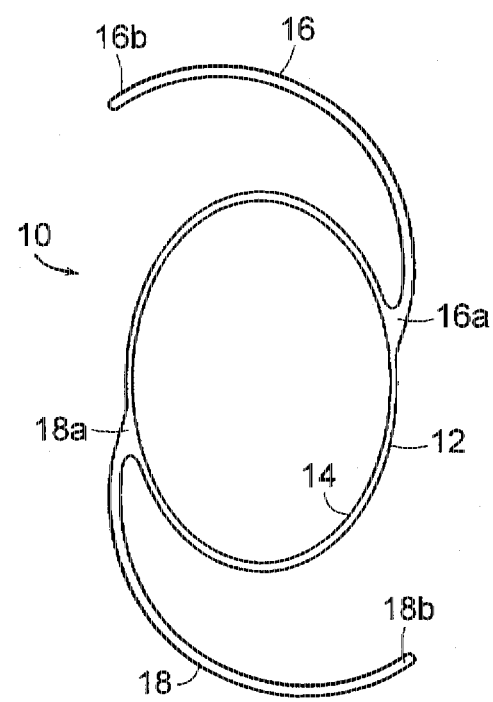
FIG. 1c is a front view of another embodiment of the haptic portion having a non-circular ring.

With reference initially to FIGS. 1 to 3, a first embodiment of the intraocular implant is described in which the optical portion is constituted by a single lens, e.g. for correcting astigmatism.

FIGS. 1a and 1b show a preferred embodiment of the haptic portion 10 of the implant. It is constituted by a ring 12 defining a circular opening 14, said ring being of small thickness and width. Two haptic loops 16 and 18 are attached at two substantially diametrically opposite points of the ring 12. A first end 16a, 18a of each loop is secured to the periphery of the ring 12 and is preferably connected thereto by means of fillets. The opposite end 16b, 18b of each haptic loop is free and bears against the inside wall of the eye when the implant is installed in the eye. FIG. 1a shows one possible shape for the loop. However, it is possible to use any conventional shape of loop or more generally of haptic portion, providing a circular opening 14 is defined.

Figures 2A, 2B:
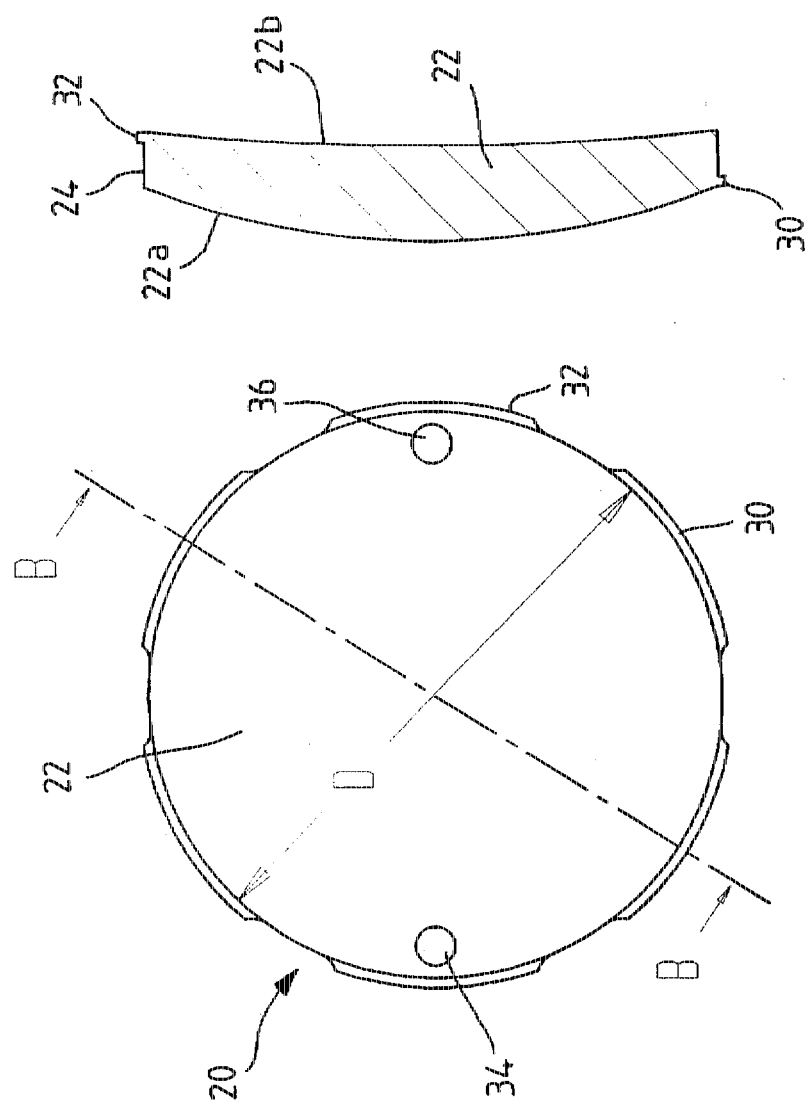
FIGS. 2a and 2b are respectively a front view and a diametral section through a lens constituting the optical portion of the implant.

FIGS. 2a and 2b show a preferred embodiment of the optical portion 20 which is constituted more specifically by a lens 22 whose periphery 24 is circular, having a diameter D equal to or substantially equal to that of the opening 14 in the haptic portion. At its periphery 24, the lens 22 has a first series of projections 30 close to the front face 22a of the lens, and a second series of projections 32 close to the back face 22b of the lens. The distance between the projections 30 and 32 is very slightly greater than the thickness of the ring 12. As already mentioned, the anterior and posterior faces 22a and 22b of the lens 22 are defined to correct astigmatism, for example, by defining a main diametral axis for correction. In its front face, the lens 22 is preferably provided with two holes 34 and 36 for orienting the optical portion 20 relative to the haptic portion 10.

FIGS. 3a and 3b show the assembled intraocular implant in full. For assembly proposes, the lens 22 is installed in the ring 12 of the haptic portion so that the projections 30 and 32 are respectively in front of and behind the ring 12. Thus the lens 22 is prevented from moving in translation in the direction of its optical axis XX' relative to the haptic portion, but it can be caused to rotate about said axis relative to the haptic portion, e.g. by means of surgical instruments cooperating with the holes 34 and 36.

Other means for preventing the lens moving in translation would consist in providing the periphery of the lens 22 with a continuous or discontinuous groove in which the inside edge of the ring 12 is engaged. Naturally, it is possible to provide for the ring 12 to have a groove in its inside face and for the periphery of the lens to be provided with radial projections that penetrate into the groove.

In order to prevent the lens 22 from rotating freely in the haptic portion, the inside face of the ring 12 defining the opening 14 preferably has two small-sized flats 40 and 42. When the lens is mounted in the ring 12, these flats provide a certain amount of friction or braking which prevents the lens rotating relative to the haptic portion unless adequate torque is deliberately applied to the lens to cause it to rotate.

Another solution consists in ensuring that, at rest, the ring 12 is not circular in shape as shown in FIG. 1c, e.g. being oval or elliptical. After the circular optical portion has been put into place, the resulting deformation of the ring serves to obtain the braking effect. It is also possible to provide for the periphery of the lens to be not accurately circular, e.g. being oval or elliptical, in which case the ring 12 can be circular in shape when at rest.

Various materials can be used for making the haptic portion and the optical portion respectively. They may be made in conventional manner out of PMMA. If it is desired to reduce the size of the incision necessary for putting the implants into place in the eye, provision can be made for the ring 12 to be foldable and for the lens 22 to be made of a flexible biocompatible material such as silicone gel or hydrogel. Naturally, under such circumstances, the haptic portion is inserted into the eye initially then the optical portion is inserted, and the surgeon must then assemble the optical portion in the haptic portion inside the eye.

As already mentioned, the above-described implant makes it possible after initial installation in the eye, e.g. in the capsular sac, and after the free ends of the haptic portion have become fixed to the inside wall of the eye, to rotate the lens so as to bring its diametral correction axis into the desired angular position, with the haptic portion remaining stationary. In other words, when correcting astigmatism, the above-described implant can enable the angular position of the correction to be adjusted exactly but it does not enable the power of the correction to be modified or adapted.

With reference to FIGS. 4a and 4b, a second embodiment of the intraocular implant is described which also makes it possible to modify the power of its correction.

The optical portion is constituted by two separate lenses 50 and 52. As in the case of FIGS. 1 to 3, the haptic portion 54 is constituted by a ring 56 defining a circular opening 58 and by two haptic loops 60 and 62. The lenses 50 and 52 are both mounted to rotate in the circular opening 58. For this purpose, the inside face of the ring 56 may have annular grooves such as 64 and 66 in which projections 68 and 70 of the lenses 50 and 52 are respectively caused to penetrate. Each lens has a second series of projections such as 72 and 74 cooperating with the outside faces of the ring 56. In this way, each of the lenses is provided with separate rotary guidance and is prevented from moving in translation along the optical axis XX'. To enable each of the lenses to rotate independently, it is possible to provide the front lens 52 with holes 80. To enable the back lens 50 to be rotated, it is also possible to provide holes in the posterior face thereof, or preferably to provide two lugs such as 82 which are themselves preferably provided with holes and which project outside the outside face of the ring 56 so as to enable them to be actuated by a surgical instrument from the anterior chamber of the eye. In this case also, braking means (not shown in the figures) are provided on the ring, e.g. flaps to prevent the lenses rotating freely when deliberate force is not being applied thereto. The braking means act separately on each of the two lenses.

Thus, by rotating both lenses together it is possible to modify the angular position of the diametral direction of correction while by modifying the relative position of the two lenses it is possible to adapt the power of the correction.

Figure 5:
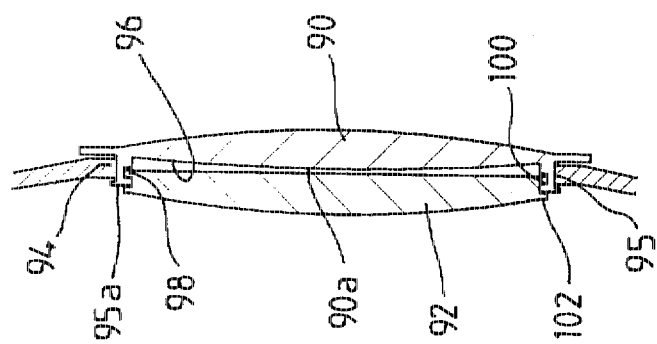
FIG. 5 is a diametral section through a first variant of the second embodiment of the implant having two lenses which are directly mounted to one another.

FIG. 5 shows a first variant of an intraocular implant having two lenses 90 and 92. In this embodiment, the lens 90 is mounted in the ring 94 of the haptic portion like the lens 22 in FIGS. 1 to 3. The anterior face 90a of the lens 90 is extended in the form of a sleeve 95 which thus defines a substantially cylindrical housing 96. The second lens 92 is mounted to rotate in said housing being guided to rotate therein. Such rotary guidance can be obtained, for example, by providing an annular groove 98 in the sleeve 95 into which projections 100 on the lens 92 can penetrate. Another series of projections 102 co-operate with the front face 95a of the sleeve 95. Separate rotary braking means are provided between the haptic portion 94 and the lens 90, and between the lens 90 and the lens 92.

Figure 6:
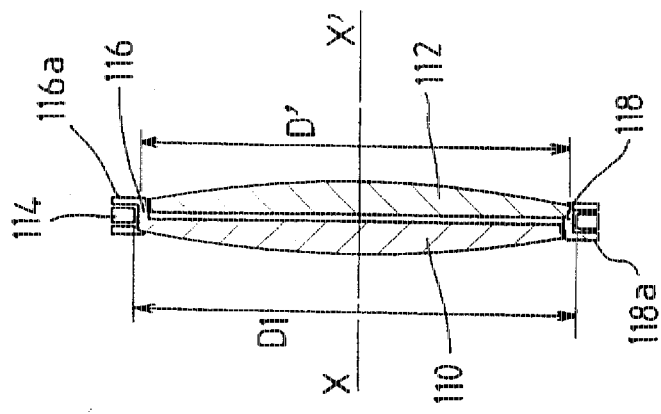
FIG. 6 is a diametrical section through a second variant of an implant embodiment having two lenses.

FIG. 6 shows a second variant embodiment of a two-lens implant. The front lens 110 and the back lens 112 are of diameter D' that is slightly smaller than the inside diameter $D_1$ of the haptic ring 114. The front lens 110 has angled radial projections 116 each having a terminal portion 116a that bears against the back face of the ring 114. Similarly, the back lens 112 has angled radial projections 118 each having a terminal portion 118a that bears against the front face of the ring 114. These projections 116 and 118 correspond to angles at the center of small value. Co-operation between the ring 114 and the two series of projections 116 and 118 serves to prevent the lenses 110 and 112 moving in translation relative to the ring 114, while nevertheless allowing relative rotation of the two lenses through an angle at the center that depends essentially on the number of projections from each lens.

It is important to emphasize that the implant could include more than two lenses mounted to rotate in the haptic portion. Under such circumstances, it is possible to give each lens surfaces that are relatively simple to machine, e.g. surfaces that are spherical, conical, toroidal, or cylindrical, with the stack of said lenses serving to build up an overall optical correction function that is relatively complex. In this case also, each lens must have holes and/or lugs to enable each lens to be rotated individually, and each lens must be associated with its own braking means.

It will be understood that in this invention, whichever embodiment is considered, the haptic portion serves solely to hold the optical portion in the eye and it does not perform any optical function. The entire correction function is performed by the optical portion of the implant.

It will also be understood that the haptic portion only surrounds the optical portion and it does not overlie it in any way. More precisely, the haptic portion, and in particular the ring 12 lies outside the field of view of the eye in which the implant is installed.

What is claimed is:

1. An intraocular implant device for correcting ocular anisotropy and in particular astigmatism, the device comprising a single optical lens and a haptic portion distinct from said optical lens, said optical lens having an optical axis and a substantially circular periphery, said optical lens having fixed shape and fixed optical properties when implanted within an eye and being suitable for correcting the anisotropy in a diametral direction, said haptic portion having a first portion suitable for cooperating with the inside wall of the eye when the implant device is disposed in the eye for the purpose of holding said optical lens in position, and a second portion suitable for cooperating with the periphery of said optical lens to define rotary guidance means for said optical lens about the optical axis, means for preventing movement of said optical lens in translation relative to said haptic portion along the optical axis, and braking means for allowing said optical lens to rotate only under the effect of applying to said optical lens a torque of magnitude greater than a predetermined value, whereby the diametral direction of anisotropy correction can be modified when the intraocular implant is disposed within the eye.

2. An intraocular implant device according to claim 1, wherein said second portion of said haptic portion is comprised of a guidance part defining a circular opening having a diameter that is substantially equal to that of the periphery of said optical lens, and wherein the periphery of said optical lens includes groove-forming means for cooperating with said guidance part.

3. An intraocular implant device according to claim 2, wherein said groove-forming means comprises radial projections at the periphery of said optical lens disposed respectively on either side of said guidance part in the direction of said optical axis.

4. An intraocular implant device according to claim 2, wherein said guidance part is comprised of an annular part having an inside periphery and an outer periphery, and wherein said first portion of said haptic portion includes at least two loops, each loop having a first end that is free and curved and a second end that is secured to said annular part.

5. An intraocular implant device according to claim 2, wherein said braking means includes the inside periphery of said guidance part being noncircular.

6. An intraocular implant device according to claim 5, wherein the inside periphery of said guidance part is elliptical or oval.

7. An intraocular implant device according to claim 5, wherein the inside periphery of said guidance part includes at least one flat.

8. An intraocular implant device according to claim 2, wherein the inside periphery of said guidance part is circular, and wherein the periphery of said optical lens is noncircular.

9. An intraocular implant device according to claim 1, wherein said second portion of said haptic portion is comprised of a guidance part defining a circular opening having a diameter substantially equal to that of the periphery of said optical lens, and wherein the guidance part includes groove-forming means for cooperating with the periphery of said optical lens.

10. An intraocular implant device according to claim 1, wherein said optical lens has a hole in one of its faces and in the vicinity of its periphery, said hole being suitable for receiving an end of an instrument for causing said optical lens to rotate relative to said haptic portion.

11. An intraocular implant device for correcting annular anisotropy, said intraocular implant device comprising:

an optical portion including n separate optical lenses (n>1), each optical lens having a common optical axis and a substantially circular periphery, each optical lens having a fixed shape and fixed optical properties when implanted within an eye and being suitable for correcting the anisotropy in a diametral direction;

a haptic portion including a first portion suitable for cooperating with the inside wall of the eye when the implant device is disposed in the eye and a second portion for cooperating with the periphery of each optical lens to define n separate rotary guidance means for said optical lenses about the common optical axis;

means for preventing movement of said optical lenses in translation relative to said haptic portion along said common optical axis; and n separate braking means for allowing each optical lens to individually rotate only under the effect of applying to each optical lens a torque of magnitude greater than a predetermined value.

12. An intraocular implant device according to claim 16, wherein each optical lens has means suitable for cooperating with a surgical instrument to enable a rotary torque to be applied to said optical lens.

13. An intraocular implant device according to claim 11, wherein each optical lens includes a surface that is spherical, conical, toroidal, or cylindrical.

* * * * *